United States Patent [19]

Huber

[11] 4,268,478
[45] * May 19, 1981

[54] METHOD AND APPARATUS FOR GENERATING AND TRANSFERRING A GASEOUS TEST SAMPLE

[75] Inventor: Bernhard W. Huber, Uberlingen, Fed. Rep. of Germany

[73] Assignee: Bodenseewerk Perkin-Elmer & Co. GmbH, Uberlingen, Fed. Rep. of Germany

[*] Notice: The portion of the term of this patent subsequent to Feb. 6, 1995, has been disclaimed.

[21] Appl. No.: 5,541

[22] Filed: Jul. 19, 1978

Related U.S. Application Data

[60] Division of Ser. No. 835,070, Sep. 21, 1977, Pat. No. 4,138,215, which is a continuation of Ser. No. 808,004, Jun. 20, 1977, abandoned.

[30] Foreign Application Priority Data

Jun. 18, 1976 [DE] Fed. Rep. of Germany ....... 2627255

[51] Int. Cl.³ ............................................ G01N 27/64
[52] U.S. Cl. .................................. 422/68; 23/230 R; 422/80; 422/81
[58] Field of Search ...................... 23/230 R, 232 R; 422/68, 80, 81, 116; 137/60, 1

[56] References Cited

U.S. PATENT DOCUMENTS

| | | | |
|---|---|---|---|
| 2,866,690 | 12/1958 | Coyne | 422/68 |
| 3,223,486 | 12/1965 | Holl, Jr. et al. | 422/68 |
| 3,271,111 | 9/1966 | Boyd, Jr. et al. | 422/81 X |
| 3,768,973 | 10/1973 | Wasilewski | 422/68 |
| 3,801,282 | 4/1974 | Manning et al. | 422/91 |
| 3,844,719 | 10/1974 | Hammitt | 422/81 |
| 3,904,371 | 9/1975 | Neti et al. | 23/232 R |
| 3,920,396 | 11/1975 | Schay | 422/68 |
| 3,923,461 | 12/1975 | Baiden | 23/232 |
| 3,929,411 | 12/1975 | Takano et al. | 422/81 |
| 4,138,215 | 2/1979 | Huber | 422/68 X |

OTHER PUBLICATIONS

Beckman Instruments Inc. Bulletin, M-2029, Jul. 1975.
E. N. Pollock et al., Atomic Absorption Newsletter, vol. 12, No. 1, Jan.-Feb. 1973, pp. 6-8.
Perkin-Elmer "Zubehor zur Flammenlosen Quecksilber-Bestimmung mit Atom Absorptions-Spektroskopie," Sep. 1973.
Perkin-Elmer "Hybrid-System," Sep. 1974.
Hatch et al., Analytical Chem., vol. 40/1968, pp.2085-2087.
Schmidt et al., Analytic Letters, 6(1), pp. 17-23 (1973).
Fernandez, Atomic Absorption Newsletter, vol. 12, No. 4, Jul.-Aug. 1973, pp. 93-97.
Chu et al., Analytical Chem., vol. 44, No. 8, Jul. 1972, pp. 1472-1479.
Thompson et al., Analyst, Sep. 1974, vol. 99, pp. 595-601.
Goulden et al., Analytical Chemistry, vol. 46, No. 11, Sep. 1974, pp. 1431-1438.

Primary Examiner—Michael S. Marcus
Attorney, Agent, or Firm—Salvatore A. Giarratana; Edwin T. Grimes; Robert A. Hays

[57] ABSTRACT

Method and apparatus for generating a gaseous test sample from a liquid sample and for transferring this test sample into a measuring cuvette of an atomic absorption spectrometer, in which an inert gas flow is directed through a sample vessel and into a measuring cuvette and, after the air has been displaced from the sample vessel, a reagent is added for generating a gaseous test sample, the test sample being carried into the measuring cuvette by the inert gas flow, wherein prior to the adding of the reagent, the flow rate of the inert gas flow is changed-over from a higher value to a lower value.

8 Claims, 6 Drawing Figures

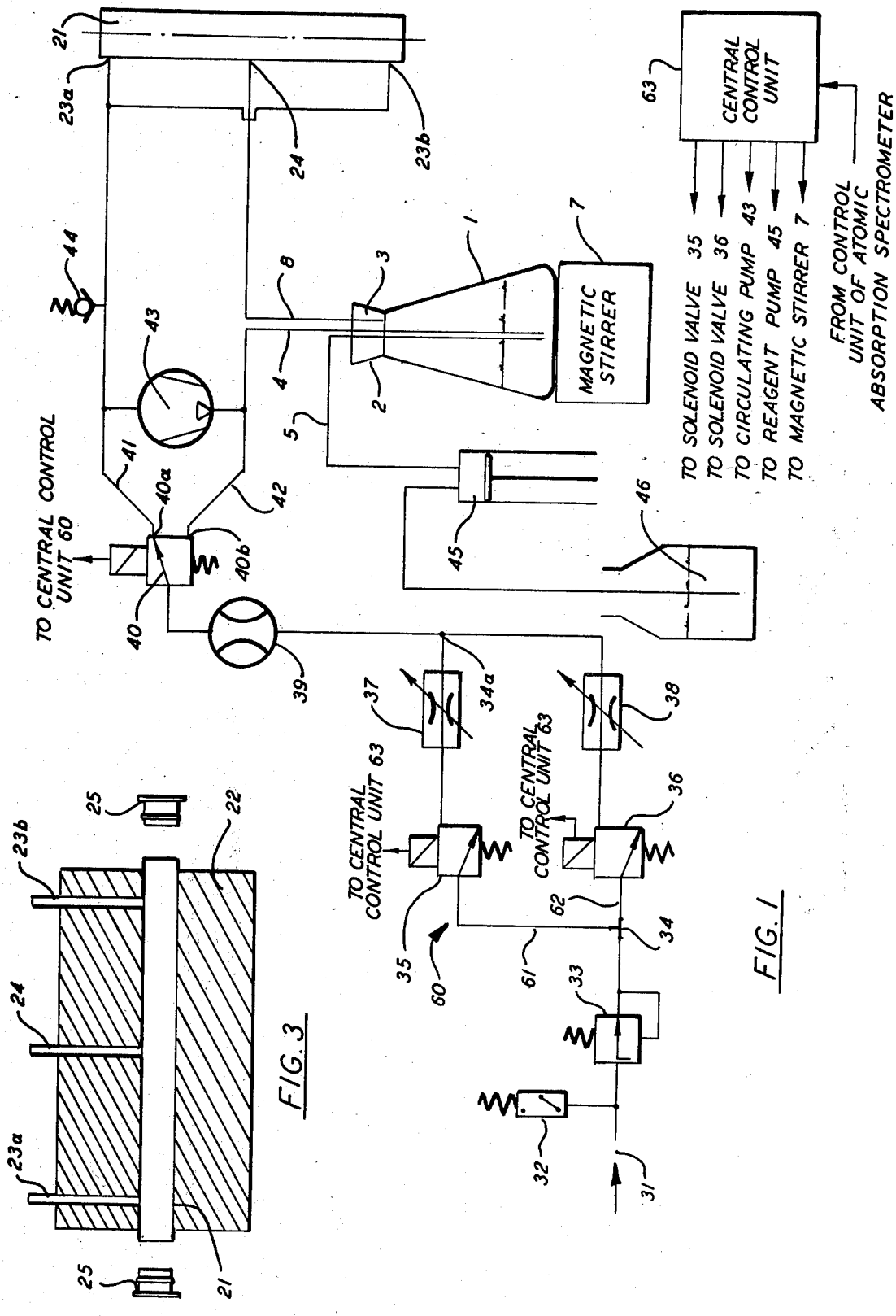

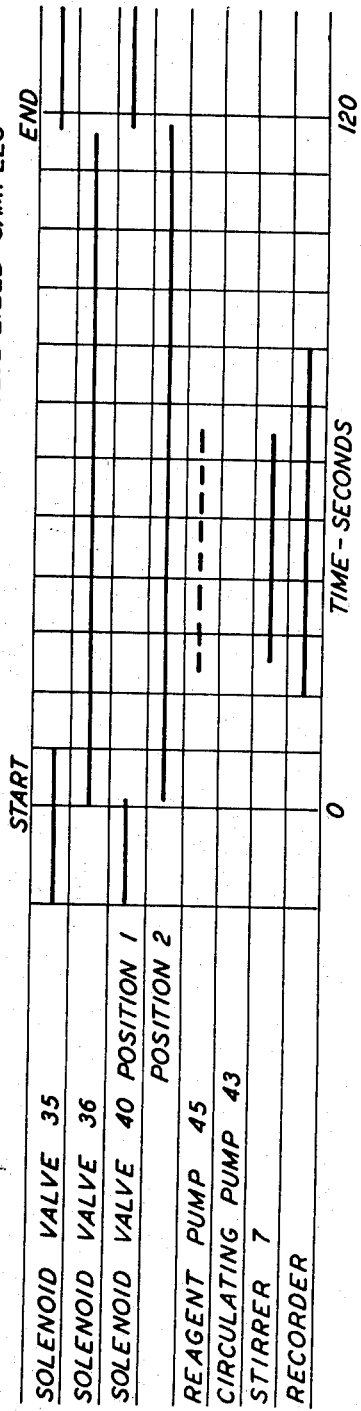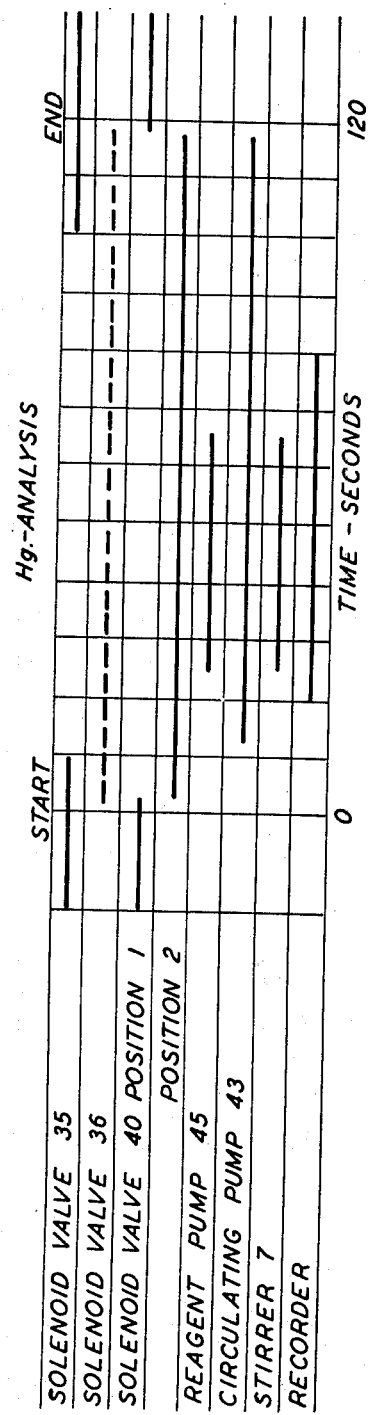

METHOD AND APPARATUS FOR GENERATING AND TRANSFERRING A GASEOUS TEST SAMPLE

BACKGROUND OF THE INVENTION

This is a division of application Ser. No. 835,070, filed Sept. 21, 1977, now U.S. Pat. No. 4,138,215 which is a continuation of U.S. application Ser. No. 808,004, filed June 20, 1977 abandoned.

FIELD OF THE INVENTION

The invention relates to a method for generating a gaseous test sample from a liquid sample and for transferring this test sample into a measuring cuvette of an atomic absorption spectrometer, in which an inert gas flow is directed through the sample vessel and into the measuring cuvette and, after the air has been displaced from the sample vessel, a reagent is added leading to the generation of the gaseous test sample, the test sample being carried into the measuring cuvette by the inert gas flow.

PRIOR ART

It is known to generate, in a sample vessel, volatile hydrides of an element from a liquid sample by adding a strong reducing agent as a reagent, when analyzing elements such as arsenic or selenium, for example. These volatile hydrides were then transferred by an inert gas flow into a heated measuring cuvette of an atomic absorption spectrometer, where they were thermally decomposed. Thus, the element was present in its atomic state in the cuvette, and its atomic absorption could be measured. However, it was also possible to release a volatile substance from its composition by the reagent, and in this case, the volatile substance was carried along by the inert gas flow so that the atomic absorption could be measured in the cuvette.

In the prior art device for carrying out this method, described in the Beckman Instruments', Inc. Bulletin, M-2029, a sample vessel with a closure plug was provided, and an inert gas inlet passage in the form of an inert gas inlet tube extended through the plug neraly to the bottom of the sample vessel. An inert gas outlet conduit and a tube for adding reagent also passed through the plug. The inert gas inlet tube was connected to an inert gas inlet port through an inlet conduit containing a shutoff valve, said inlet port being supplied from a source of inert gas such as argon, for example. The inert gas outlet conduit led from the sample vessel to a heating tubular measuring cuvette. The cuvette was closed at its ends by windows, and the inert gas outlet conduit was connected to one end, while a gas outlet port was provided at the other end. A directional control valve was mounted in the inert gas outlet conduit to optionally connect the inert gas outlet conduit to the cuvette or to establish direct communication between the inert gas inlet port and the cuvette. The tube for adding reagent was connected to a reagent pump. In addition, a stirring device in the form of a magnetic stirrer was provided.

For carrying out an analysis, the inert gas flow was first directed through the inert gas conduit, through the sample vessel and through the cuvette, so that these elements were flushed with the inert gas, and the air was displaced from the system. By actuation of the reagent pump reagent such as $NaBH_4$, for example, was added to the sample liquid, whereby a volatile test sample such as $AsH_3$, for example, was generated. This volatile test sample was transferred by the inert gas flow into the heated measuring cuvette where it was thermally decomposed, so that a "cloud" of the element under investigation, in an atomic state, was formed in the measuring cuvette. When the sample vessel was removed, such as for example, in order to replace it by a sample vessel containing another liquid sample, the shutoff valve in the inert gas inlet conduit was closed and the directional control valve was changed-over to provide direct communication between the inert gas inlet port and the inert gas outlet conduit to thereby supply inert gas to the cuvette, with the sample vessel being by-passed and the communication between the sample vessel and the cuvette being shut off. Thus, inert gas always flowed through the measuring cuvette, whereby no air could enter and generate interfering signals, or the like.

In this prior art arrangement, a single inert gas source had to perform two functions: it served to displace the air originally present in the system, and it served to transfer the generated volatile test sample from the sample vessel into the measuring cuvette. It will be appreciated that in order to displace the air from the system, the flow rate of the inert gas should be as high as possible to flush the air out of the system as quickly and thoroughly as possible. However, to transfer the test sample from the sample vessel into the measuring cuvette, the flow rate of the gas should not exceed a certain lower value in order to prevent undesirable dilution of the test sample by the inert gas, because such dilution reduces the signal level of the atomic absorption measurement. A further disadvantage of the prior art arrangement is that the actuation of the apparatus had to be manually effected. Automation of the measurement procedure was not possible with the prior art arrangement.

In the prior art arrangement, reagent was added in liquid form. However, in many cases, it is desirable to add a solid reagent, such as metal chips or sodiumboronhydride in lozenge form, for example. It is well known to insert such solid reducing agents into the sample vessel through an opening provided therefor, by temporarily opening the sample vessel, after the whole device has been flushed with inert gas, as described in "Atomic Absorption Newsletter", Vol 12, No. 1 (1973), P. 6. When a system which has already been filled with inert gas is subsequently opened, there is a risk of air leaking back into the system. Such air, together with the hydrogen, which is developed by the addition of the reducing agent, forms an undesirable and inflammable mixture. In addition, the air itself generates an absorption signal, which interfers with the determination of arsenic, for example.

It is also well known, for analyzing mercury, to transport the monatomic mercury contained or formed in a liquid sample by an air flow through a measuring cuvette in a closed system by means of a circulating pump. The prior art apparatus is described in the Perkin-Elmer Corporation brochure, 10 066-9, 73, entitled "Perkin-Elmer Zubehör zur flammenlosen atom-absorptions-spektroskopie", contained a sample vessel with a closure plug. A gas inlet tube passed through the closure plug and extended nearly down to the bottom of the sample vessel and ended there in a "bubble generator" which fed the entering gas, suspended in fine bubbles, into the liquid sample. A gas outlet conduit, which also passed through the closure plug, connected the interior of the sample vessel with one end of the tubular measuring cuvette, which was closed at the ends by windows. The other end of the cuvette was connected to the inlet port of a circulation pump. The discharge port of the circulation pump was connected to the gas inlet tube.

With this prior art arrangement, the mercury was driven out of the liquid sample by the air flow generated by the circulation pump, and the mercury vapor was directed through the measuring cuvette. After about 30 seconds, a state of saturation was reached in which the mercury concentration in the cuvette was measured.

SUMMARY OF THE INVENTION

A basic and general object of the invention resides in the provision of a new and improved method and apparatus for generating and transferring a gaseous test sample, which overcomes or at least mitigates some of the problems of the prior art, as outlined hereinabove.

It is another object of the invention to provide a method and apparatus for generating and transferring a gaseous test sample, which effects rapid and efficient flushing of the system with inert gas, and which provides an optimum measuring signal.

A further object of the invention is to provide control means for permitting the analysis to be carried out automatically.

Another object of the invention is to provide a device which permits the analysis of volatile test samples such as, for example, volatile hydrides thermally decomposed in the measuring cuvette in an open system, and which also permits working in a closed system mode.

A further object of the invention is to provide a device of the type described, which permits the addition of a solid reagent at a predetermined moment, after the air has been displaced by the inert gas, without the system having to be opened again.

According to an important feature of the invention, the flow rate of the inert gas flow is changed-over from a higher to a lower value prior to the addition of the reagent. That is, the apparatus is flushed with a relatively large inert gas flow, and then a smaller gas flow serves to transfer the volatile test sample after reagent has been added, to thereby reduce the dilution of the test sample by the inert gas and, as a result, provide a stronger measuring signal.

In one form of the invention, there is provided a new and improved device for generating a gaseous test sample from a liquid sample and for transferring this test sample into a measuring cuvette of an atomic absorption spectrometer, which comprises: a sample vessel, a closure plug for closing the sample vessel, an inert gas inlet passage means and an inert gas outlet passage means which pass through said plug. In addition, there is provided inert gas inlet conduit means for connecting the inert gas inlet passage means to an inert gas source. Means are provided for adding reagent to the sample vessel and means are provided for stirring the sample vessel. The inert gas outlet conduit is arranged to form permanent fluid flow communication between the sample vessel and the measuring cuvette. The inert gas inlet conduit means includes means for providing a first rate of flow of inert gas and a second substantially lower rate of flow of inert gas, and a solenoid control valve assembly is provided for changing-over between the first flow rate and the second flow rate. Control means are provided for automatically controlling the solenoid valve assembly, said means for adding reagent, and said means for stirring said sample vessel, in a predetermined timed sequence with respect to each other.

Such a device permits the analysis to be carried out automatically. This is made possible by the fact that the valve assembly is uniquely located upstream of the sample vessel and, therefore, only pure inert gas flows therethrough. The test sample does not flow through this valve assembly. As a result, the valve assembly can be constructed with ordinary solenoid valves, as they are not subjected to chemical corrosion by the test sample.

According to one aspect of the invention, the means for providing a first and a second rate of flow of inert gas comprises a pair of branch lines operative in parallel relationship. The first branch line contains a first restriction means and the second branch line contains a second restriction means. The solenoid assembly comprises a first solenoid valve mounted in the first branch line and a second solenoid valve mounted in the second branch line. As a result, the solenoid valve assembly for changing-over the inert gas flow can be constructed with simple, fully opened or completely closed solenoid valves. Accurate adjustment may be effected by the selection or adjustment of the associated flow restriction means.

According to another aspect of the invention, the inert gas inlet conduit means comprises a three port-two directional solenoid control valve having an inlet port connected to receive inert gas from the pair of branch lines and having a first outlet port connected to the inert gas inlet passage means in fluid flow relationship. A connecting conduit is provided for connecting a second outlet port of the three port-two directional control valve to the measuring cuvette. The control means serve to actuate the control valve to connect the inlet port to the first outlet port in a first valve position and to connect the inlet port to the second outlet port in a second valve position. That is, the three port-two directional control valve is switched to its first valve position between analyses and to its second valve position for the duration of each analysis.

Preferably, a large inert gas flow is directed to the cuvette between the analyses, when one sample vessel is being replaced by another. Thus, the measuring cuvette remains permanently filled with inert gas. In contrast to the directional control valve of prior art apparatus, the three port-two directional control valve is only subjected to pure inert gas and as a result, a conventional solenoid valve may be employed. The leakage of air through the inert gas outlet conduit, while the sample vessel is removed, is prevented by the large inert gas flow fed to the cuvette.

According to another feature of the invention, the cuvette is in the form of a tubular body having open ends. The tubular body has a medial first port connected to the inert gas outlet conduit, and a second port located at one end thereof connected to the connecting conduit. In addition, the tubular body has a third port located at the other end, and means are provided for connecting the third port to the second port in fluid flow communication externally of the tubular body. As a result, windows which tend to interfere with the absorptions or in reflecting losses, can be omitted. The inert gas flow forms a "curtain" in front of the ends of the measuring cuvette, which prevents the air from leaking in. According to still another feature of the invention, the sample vessel is detachably attachable to the closure plug, which is mounted in a stationary manner in the device. The reagent adding means and the means for stirring the sample vessel are mounted on this closure plug. Thus, the various sample vessels with the liquid samples may be attached in a simple manner, consecutively to a single stationary closure plug.

As another feature of the invention, the means for stirring the sample vessel include a magnetic stirrer having a stirring body containing a permanent magnet, the magnetic stirring being driven by a rotating magnetic field. The means for adding the reagent to the sample vessel include: a tray for receiving solid reagent, such tray being connected to the stirring body, whereby the reagent is flung from the tray into the liquid sample by virtue of centrifugal force, when the stirring body rotates. With such an arrangement, the reagent adding device is combined with the stirring device.

As one other feature of the invention, the inert gas inlet passage means comprises an inert gas inlet tube extending nearly to the bottom of the sample vessel. A block-like member, attached to the inert gas inlet tube, has a lower end face disposed adjacent the bottom of the sample vessel, said lower end face having a circular recess into which the inert gas inlet tube opens. This block-like member has an upper end face tapered inwardly and downwardly to form a cup-shaped receptacle for receiving solid reagent. The block-like member is provided with a vertically disposed outer passage extending from a opening adjacent the periphery of the recess to an opening disposed adjacent the upper outer edge of the receptacle. Also, the block-like member has a vertically disposed medial passage for providing fluid flow communication between a lower medial portion of the receptacle with said recess. The means for stirring the sample vessel include a magnetic stirrer having a stirring body loosely held between the peripheral rim of the recess and the bottom of the sample vessel. A permanent magnet is carried by the stirring body and the magnetic stirrer is driven by a rotating magnetic field. In this embodiment, the reagent adding device is combined with the stirring device, and the magnetic stirrer acts, at the same time, as a centrifugal pump, by means of which the liquid is pumped over the reagent.

According to still another feature of the invention, the measuring cuvette is closed by detachably mounted windows disposed in the path of the rays of radiation during spectrophotometric measurement. The cuvette has a first port in fluid flow communication with the inert gas conduit means and at least one second port offset with respect to the first port in the direction of the path of the rays of radiation. The second port is connected to the inert gas inlet passage means through a circulation pump. It will thus be appreciated that the same apparatus may be used, optionally, for the analysis of arsenic, or the like, in an open system, and for the analysis of mercury, or the like, in a circulation mode.

There has thus been outlined rather broadly, the more important features of the invention in order that the detailed description thereof that follows may be better understood and in order that the present contribution to the art may be better appreciated. There are, of course, additional features of the invention which will be described more fully hereinafter. Those skilled in the art will appreciate that the conception on which this disclosure is based may readily be utilized as the basis of designing other methods and devices for carrying out the various purposes of the invention. It is important, therefore, that this disclosure be regarded as including such equivalent methods and devices as do not depart from the spirit and scope of the invention.

Several embodiments of the invention have been chosen for purposes of illustration and description and are shown in the accompanying drawings forming a part of this specification.

BRIEF DESCRIPTION OF THE DRAWINGS

FIG. 1 is a schematic diagram showing a device for generating a gaseous test sample from a liquid sample and for transferring this test sample into a measuring cuvette, according to the invention;

FIGS. 2A and 2B are timing diagrams showing the interrelationship of the various elements during an operating cycle;

FIG. 3 is an enlarged, medial, sectional view of a measuring cuvette for the device of FIG. 1;

DETAILED DESCRIPTION OF THE PREFERRED EMBODIMENTS

Figure 4:
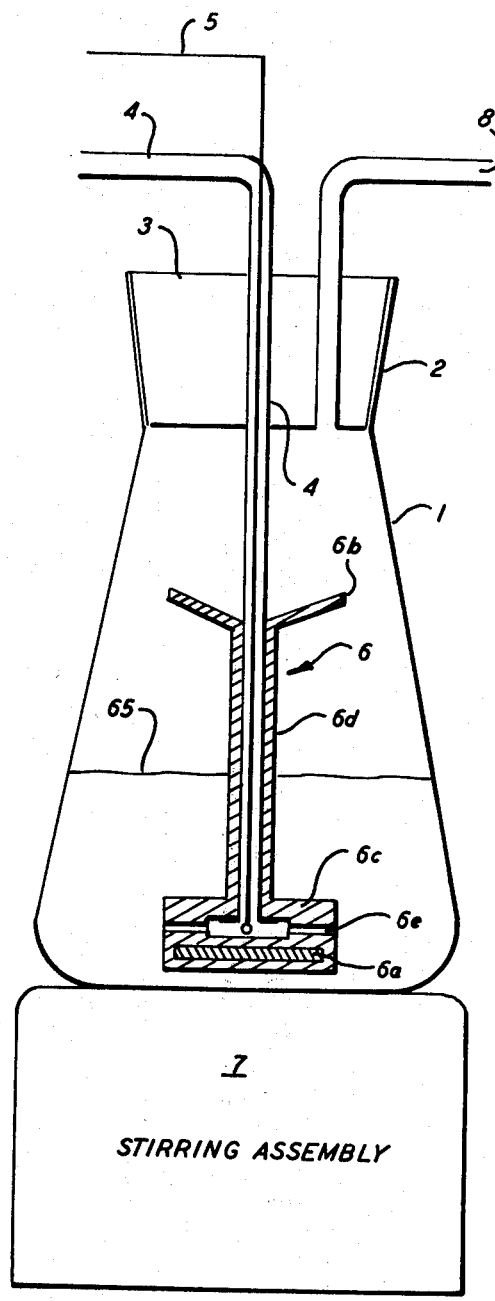
FIG. 4 is an enlarged medial, sectional view, partly in block diagram form, of a sample vessel, showing the reagent adding device for solid reagents.

In the embodiment of the invention illustrated in FIG. 1, a sample vessel 1 is mounted on a magnetic stirring assembly 7. The sample vessel may be, for example, an Erlenmeyer flask having a conical, ground-glass neck 2. This sample vessel is removably attachable in sealed relationship to a fixedly mounted closure member or plug 3 of mating configuration, and an inert gas inlet passage means, which includes a tube 4, extends through the closure plug 3, with the outer end thereof being connected to an inert gas inlet conduit 42, leading to an outlet port 40b of a solenoid three port-two directional control valve 40. A coaxially disposed inner tube 5 is mounted inside the tube 4 and both tubes extend downwardly towards the bottom of the sample vessel 1. Above the sample vessel 1, the inner tube 5 passes through the wall of the outer tube 4 and is connected to the outlet of a reagent pump 45, the inlet of the reagent pump being connected to a supply vessel 46, containing a suitable reagent liquid.

Still referring to FIG. 1, the closure member 3 has a second passage therethrough for receiving an inert gas outlet conduit 8, which at the lower end thereof is flush with the inner edge of the closure member or plug 3. The other end of the inert gas outlet conduit 8 is connected to the central port 24 of a heatable measuring cell or cuvette 21. The cuvette 21 has two outlet ports 23a and 23b at the ends thereof, respectively, which are connected to each other and thence, through a connecting conduit 41 to a second outlet port 40a of the solenoid control valve 40. The connecting conduit 41 includes a vent valve 44, and a circulating pump 43 is connected between the connecting conduit 41 and the inert gas inlet conduit 42.

Inert gas inlet conduit means serve to connect the inert gas inlet conduit 42 to an inert gas source. This system includes: an inlet terminal 31 connected to a suitable inert gas source (not shown), a pressure monitor 32, a pressure reducer 33 and flow restriction means indicated generally at 60, which are mounted downstream of the pressurized gas terminal 31. A flow meter 39 is mounted between the outlet of the flow restriction means 60 and the inlet port of the three port-two directional control valve 40. The flow restriction means 60 includes two parallel branch lines 61 and 62 connected between an inlet T-connection 34 and an outlet T-connection 34a. The first branch line contains a solenoid control valve 35 and a preadjusted fine regulating valve 37 mounted in series, while the second branch line contains a solenoid control valve 36 and a preadjusted fine regulating valve 38, also mounted in series.

In operation, the regulating valve 37 is wide open while the regulating valve 38 is only slightly opened, whereby when the solenoid valves 35 and 36 are both opened, or when only the solenoid 35 is opened, a gas flow is generated which is sufficient to flush the whole apparatus with inert gas. When the solenoid valve 36 is opened and the solenoid valve 35 is closed, there is a smaller flow of inert gas, which is sufficient to transport the gaseous test sample from the sample vessel 1 to the cuvette 21, but which is sufficiently small that the flow rate of the inert gas does not disadvantageously affect the measuring sensitivity.

It will be appreciated that the solenoid valves 35, 36 and 40 are controlled by a central control unit 63. In addition, the circulation pump 43 and the reagent pump 45, as well as the magnetic stirrer 7 are also controlled by this control unit. The central control unit is, in turn, controlled by the control unit of the atomic absorption spectrometer (not shown) in a conventional manner.

As a result, a programmed sequence of the individual steps for carrying out an analysis with the apparatus as described, is effected.

FIG. 2A illustrates in diagrammatic form the timing sequence of the individual elements during a programmed operational cycle using the apparatus of FIG. 1. This figure shows the analysis in an open mode of operation. That is, the measuring cuvette in most cases is opened at its ends and the circulating pump 43 is out of operation. However, in some installations, the cuvette 21 may be closed at its ends, with the venting of the sample gas being effected through the vent valve 44.

In order to start the apparatus, the solenoid valve 40 is switched in such a way as to connect the inlet port with the second outlet port 40a so that inert gas flows through the whole apparatus including the measuring cuvette 21, but excluding the sample vessel 1 and the branches communicating therewith. At the start of the program, the solenoid valve 36 is opened and the solenoid valve 40 is switched-over to its second position so that its inlet port is connected to the first outlet port 40b, whereby the inert gas flow is directed through the inert gas inlet conduit 42 into the liquid sample disposed within the sample vessel 1, and thence back out through the inert gas outlet conduit 8 to the central port 24 of the measuring cuvette 21. Further venting of the flushing gas is then effected, as described hereinbefore. After 10 seconds, the solenoid valve 35 is closed so that only a reduced inert gas flow is directed to the sample vessel, as required, for carrying out the analysis. At this time, the analytical instrument is switched-on in preparation for measurement. After about 20 seconds, the recorder of the instrument is also switched-on. After about 25 seconds, the apparatus is ready for measurement and the reagent pump 45 and the stirrer assembly 7 are switched-on. Reagent is delivered to the reagent adding tube 5 and enters the liquid sample contained in the sample vessel 1, where it is intensely mixed due to the action of the magnetic stirrer assembly 7. During this time, gas is generated, which is carried along by the inert gas entering through the inlet tube 4 and exiting through the inert gas outlet conduit 8, so that it reaches the measuring cuvette 21 through the central port 24. After a further 40 seconds have elapsed, the analysis is finished and the reagent pump 45 and the stirrer assembly 7 are switched-off. After an additional 15 seconds, the recorder of the analytical instrument is switched-off. The flow of inert gas through the sample vessel and thence to the cuvette is continued for 30 to 40 seconds more and, thereafter, the three port-two directional control valve 40 is switched to connect its inlet port to its second outlet port 40a and, thereby direct the flow of inert gas through the connecting conduit 41 directly to the cuvette 21. At this time, the magnetic stirrer 7 and the sample vessel 1 may be removed from the closure plug 3, while the cuvette 21 is being flushed. It will be appreciated that the cuvette can remain in its operative position, as the inert gas atmosphere is still maintained. After the sample vessel 1 has been removed, the procedure may be repeated with another test sample.

It is noted that the actuation of the reagent pump 45 is illustrated by a broken line in FIG. 2a, because, as indicated hereinbefore, the operation of this pump may be dispensed within installations utilizing a solid reagent.

An analysis, which is carried out in the manner described, may be employed, for example, to determine the arsenic in solubilized samples, with the reagent liquid being, for example, a solution of sodium borohydride.

FIG. 2B illustrates the timing sequence of a cycle, when operating the system in a closed mode. The initial portion of the cycle is the same as that previously described in connection with the cycle of FIG. 2A, wherein the measuring cuvette 21 is supplied with inert gas through the opened solenoid valves 35 and 40 and through the connecting conduit 41. Then, the three port-two directional control valve 40 is switched to pass inert gas through the inert gas inlet conduit 42 to the sample vessel 1. Thereafter, the solenoid valve 35 and also, finally, the solenoid valve 36 are closed and the circulating pump 46 is started. After a short time interval, the reagent pump 35 and the stirrer 7 are switched-on, whereby the desired reaction takes place in the sample, contained in the sample vessel 1, and the gas generated is introduced into the cuvette 21 via the inert gas outlet conduit 8 and the central port 24 by means of the inert gas flow which is supplied from the inert gas inlet passage means 42. After conclusion of the measurement, the reagent pump and the stirrer assembly are switched-off, while the circulation pump 43 continues to run for some time. Thereafter, the three port-two directional control valve 40 is switched to its first position, the circulating pump 43 is switched-off and the solenoid valve 35 is again switched-on, thereby flushing the measuring cuvette 21 through the connecting conduit 41. This disconnects the sample gas circulation loop so that the stirrer assembly 7 and the sample vessel 1 may be removed from the apparatus. After another sample has been prepared, another measuring vessel 1 may be connected to the closure plug 3, whereupon the stirrer assembly 7 is again moved into place and the program as described above may be repeated.

The closed mode of operation is particularly suitable for the determination of mercury, wherein the reagent liquid added may be a solution of tin (II) chloride.

FIG. 3 shows details of the measuring cuvette 21. This cuvette has a central gas port 24 to which the inert gas outlet conduit 8 is connected. The second and third ports 23a and 23b are disposed towards the opposite ends of the cuvette, respectively. The open ends of the measuring cuvette 21 are adapted to be closed in a gas tight manner by optical windows 25, in order to permit operation of the system in the closed mode. The measuring cuvette is mounted in a heating jacket 22 for purposes of heating it to the required measuring temperature. In the arsenic analysis, as described hereinbefore, such measuring temperature is about 700° C. and in the mercury analysis, as described hereinbefore, it is about 110° C.

Referring next to FIG. 4, details of the sample vessel 1 are illustrated. The sample vessel is placed on the stirring assembly 7 and the upper end or neck thereof is removably attached to the closure plug 3 in sealed relationship by virtue of the ground-glass joint 2. A stirring body 6 is mounted for rotation about the axis of the concentric tubes 4 and 5. This body includes an upper portion 6b which is located above the liquid level 65 in the sample vessel 1 and is of cup-shaped configuration to form a tray, which is adapted to receive solid reagent. That is, the upper surface of the upper portion 6b is provided with a downwardly, inwardly inclined surface. The upper portion 6b is connected to a lower portion 6c by means of an intermediate portion 6d. The lower portion 6c is located towards the bottom of the sample vessel and is provided with a transversely extending throughbore 6e, which receives the opened ends of the concentric tubes 4 and 5. The lower portion 6c of the stirring body contains a permanent magnet 6a, and the stirring assembly 7 serves to provide a magnetic field which acts in conjunction with the permanent magnet 6a to rotate the stirring body 6 about the axis of the concentric tubes 4 and 5.

In some installations, only liquid reagents are employed, which are applied to the liquid sample through the inner tube 5, while in other installations, both liquid reagent and solid reagent are employed. In still other installations, only solid reagent is utilized. In operation, when only solid reagents are employed or when solid reagents in combination with liquid reagents are employed, the solid reagent is placed on the cup-shaped upper portion of the body 6 prior to connecting the sample vessel 1 to the closure plug. After the sample vessel 1 is connected to the closure plug 3, the analysis program as described hereinbefore is initiated. When the stirrer assembly 7 is switched-on, the stirring body 6 rotates rapidly about the axis of the concentric tubes 4 and 5 to project or fling the solid reagent circumferentially from the upper cup-shaped portion 6b by means of centrifugal force, to thereby mix the reagent with the liquid sample located in the sample vessel. The inert gas passing at a reduced flow rate through the second port 40b of the three port-two directional valve 40 passes through the conduit 42, through the tube 4, into the transverse passage 6e and thence emerges into the liquid sample at the bottom of the sample vessel. By virtue of the cooperation of the stirring body 6 and the transverse throughbore 6e, intense mixing of the sample liquid with the inert gas takes place so that the gas passing out through the inert gas outlet conduit 8 to the port 24 of the measuring cuvette 21 carries the gaseous test sample therewith.

Figure 5:
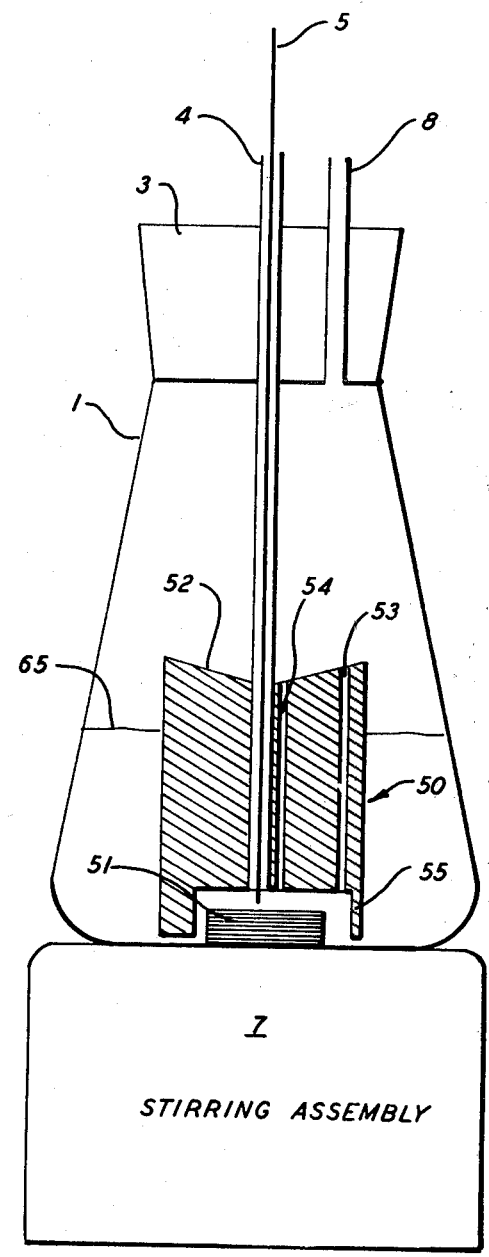
FIG. 5 is an enlarged medial sectional view similar to FIG. 4, but showing another embodiment of a reagent adding device for solid reagents for use in the device of FIG. 1.

FIG. 5 shows a second embodiment of a reagent adding device for solid reagents, according to the invention. This reagent adding device is rigidly connected to the inert gas inlet tube 4 and includes a block-like member or body 50. This block-like member has an upper face, which is tapered downwardly and inwardly to form a cup-shaped receptacle 52 for receiving the solid reagent. The lower face of the block-like member 50 is disposed adjacent the bottom of the sample vessel and is provided with a circular recess 55 into which the inert gas inlet tube 4 opens. A stirring body 51 is loosely held between the peripheral rim of the recess 51 and the bottom of the sample vessel, and a permanent magnet is carried by the stirring body. The stirring body rotates by virtue of a rotating magnetic field effected by the stirring assembly 7. The block-like member 50 has a vertically disposed outer passage or bore 53, which extends from an opening adjacent the periphery of the recess to an opening adjacent the upper, outer edge of the cup-shaped receptacle portion 52. In addition, the block-like member has a vertically disposed medial or inner passge 54 for providing fluid-flow communication between the lower medial portion of the cup-shaped receptacle 52 and the recess 55.

In operation, after the solid reagent has been placed in the cup-shaped receptacle 52 of the member 50, the sample vessel 1 is connected to the closure plug 3. Then, the analysis program, as described hereinbefore, is initiated. After the stirring assembly 7 has been switched-on, the stirring body 51 rotates within the recess 55 of the member 50 so that a centrifugal pump-like effect is produced to deliver the liquid sample upwardly through the outer axial passage 53 to the cup-shaped receptacle 52, where it contacts the reagent to produce the desired reaction. The liquid sample then flows down through the second or inner passage 54 carrying portions of the solid reagent, which are then mixed intensely with the remaining liquid sample. This mixing action is also assisted by the flow of inert gas emerging from the inert gas inlet tube 4. The flow of inert gas also carries the generated gaseous test sample through the inert gas outlet conduit 8 to the central port 24 of the measuring cuvette 21. It is noted that the reagent adding device of FIG. 5 may be utilized for the use of liquid reagent, the additions being made through the reagent adding tube 5, or the device may be utilized with only solid reagents. In addition, the device of FIG. 5 may be used for a combination of solid and liquid reagents.

The reagent adding devices illustrated in FIGS. 4 and 5 may be employed with a number of different types of solid reagents such as, for example, tablets of sodium-borohydride, or with turnings of magnesium.

It will be appreciated that the apparatus as described hereinbefore is designed so that it may be controlled in a programmed manner, the operator merely being required to interchange sample vessels. It is noted that the sample vessel need not be reopened for the purpose of adding solid reagents. The combination of the concept of adding solid reagents in cooperation with the stirring feature enables the addition of the reagent to be effected in a controlled manner at a predetermined moment, in a manner similar to that employed with the use of a liquid reagent. The central control unit of the device permits integration with the control means of the analytical instrument so that a completely pre-programmed sequence may be employed for the determination of such elements as will form volatile and thermally decomposable hydrides, or which may be transformed into such volatile forms that are amenable to such measurement. Such a programmed sequence has a particular importance in view of serial investigations required for environmental purposes, since some of the elements to be determined are extremely poisonous and continuous monitoring of their presence may be desirable.

Having thus described the invention with particular reference to the preferred forms thereof, it will be obvious to those skilled in the art to which the invention pertains, after understanding the invention that various changes and modifications may be made therein without departing from the spirit and scope of the invention, as defined by the claims appended hereto.

What is claimed is:

1. A device for generating a gaseous test sample from a liquid sample and for transferring this test sample into a measuring cuvette of an atomic absorption spectrometer comprising:
   a measuring cuvette;
   a sample vessel;
   inert gas inlet passage means and an inert gas outlet conduit, each having one end respectively in fluid flow communication with the interior of said sample vessel;
   inert gas inlet conduit means for connecting said inert gas inlet passage means to an inert gas source;
   said inert gas outlet conduit being arranged to form fluid flow communication between the interior of said sample vessel and said measuring cuvette;
   said inert gas inlet conduit means including a pair of branch lines disposed in operative parallel relationship, the first branch line containing first restriction means and the second branch line containing second restriction means, first valving means for selectively directing the flow of inert gas to one or the other or both of said branch lines to thereby selectively provide a first flow rate of gas and a second substantially lower rate of flow of inert gas;
   control means for automatically controlling said first valving means; and
   means for adding a reagent to said sample vessel.

2. A device according to claim 1 wherein said second restriction means has substantially greater restrictive characteristics then said first restriction means.

3. A device according to claim 1 wherein said inert gas inlet conduit means comprises a three port-two directional control valve having an inlet port connected to receive fluid from said pair of branch lines and having a first outlet port connected to said inert gas inlet passage means in fluid flow relationship, a connecting conduit for connecting a second outlet port of said three port-two directional control valve to said measuring cuvette, said control means serving to actuate said control valve to connect said inlet port to said first outlet port in a second valve position and to connect said inlet port to said second outlet port in a first valve position.

4. A device according to claim 3, wherein said measuring cuvette comprises a tubular body having open ends, said tubular body having a medial first port connected to said inert gas outlet conduit;
   said tubular body having a second port located at one end thereof connected to said connecting conduit;
   said tubular body having a third port located at the other end thereof; and
   means for connecting said third port of the tubular body to said second port of the tubular body in fluid flow communication externally of said tubular body.

5. A device according to claim 4 wherein said control means further controls said three port-two directional control valve, whereby said device is operatively controlled in predetermined consecutive time sequence so that;
   (a) said first valving means is switched to its position for allowing a large inert gas flow and said three port-two directional control valve is switched to its first valve positon to allow a large inert gas flow through said connecting conduit to said measuring cuvette;
   (b) the three port-two directional control valve is switched to its second valve position;
   (c) the first valving means is switched to its position for allowing a substantially lower rate of flow of inert gas;
   (d) after conclusion of the measurement, the first valving means changes the inert gas flow to a higher value and the three port-two directional control valve is returned to its first valve position.

6. A device according to claim 3 wherein said measuring cuvette is of tubular configuration closed at its ends by detachably mounted windows disposed in the path of the rays of radiation during spectrophotometric measurement, said measuring cuvette having a centrally disposed first port in fluid flow communication with said inert gas outlet conduit means, a second port disposed towards one end of said measuring cuvette, and a third port disposed towards the other end of said measuring cuvette in fluid flow communication with said second port externally of said cuvette, a circulating pump interposed between said connecting conduit and said inert gas inlet passage means, said second and third ports of said cuvette being connected in fluid flow communication with the second port of said three port-two directional control valve when said control valve is in its first position.

7. A device according to claim 6 wherein a vent valve is mounted in the connecting conduit between said circulating pump and said second and third ports of said measuring cuvette.

8. A device according to claim 6 wherein said control means further controls said three port-two directional control valve, whereby said device is operatively controlled in predetermined consecutive timed sequence so that;
   (a) said first valving means is switched to its position for allowing a large inert gas flow and said three port-two directional control valve is switched to its first valve position to allow a large inert gas flow through said connecting conduit to said measuring cuvette;
   (b) the three port-two directional control valve is switched to its second valve position to allow a large inert gas flow through said inert gas inlet passage means to said sample vessel;
   (c) the first valving means shuts off the inert gas flow or changes it over to a smaller value;
   (d) the circulation pump is switched on;
   (e) after conclusion of the measurement, the first valving means changes the inert gas flow to a higher value;
   (f) the circulation pump is switched off and the three port-two directional control valve is returned to its first valve position.

* * * * *